United States Patent [19]

Dahl et al.

[11] Patent Number: 5,531,779
[45] Date of Patent: Jul. 2, 1996

[54] STENT-TYPE DEFIBRILLATION ELECTRODE STRUCTURES

[75] Inventors: Roger W. Dahl, Andover; Robert W. Wickham, deceased, late of Harris, both of Minn., by Duane Quiggle, administrator; David K. Swanson, Roseville, Minn.; David Lipson, Poway, Calif.

[73] Assignee: Cardiac Pacemakers, Inc., St. Paul, Minn.

[21] Appl. No.: 377,494

[22] Filed: Jan. 24, 1995

Related U.S. Application Data

[63] Continuation of Ser. No. 243,656, May 16, 1994, abandoned, which is a continuation of Ser. No. 955,166, Oct. 1, 1992, abandoned.

[51] Int. Cl.[6] ................................................. A61N 1/39
[52] U.S. Cl. ........................... 607/119; 607/5; 607/122; 128/642
[58] Field of Search .................... 607/116, 119, 607/122–125; 606/45, 191, 194, 195, 198; 128/642; 604/21; 623/1

[56] References Cited

U.S. PATENT DOCUMENTS

| | | |
|---|---|---|
| 3,664,347 | 5/1972 | Harmjanz . |
| 3,737,579 | 6/1973 | Bolduc . |
| 3,749,101 | 7/1973 | Williamson . |
| 3,788,329 | 1/1974 | Friedman . |
| 3,942,536 | 3/1976 | Mirowski et al. . |
| 4,291,707 | 9/1981 | Heilman et al. . |
| 4,522,212 | 6/1985 | Gelinas et al. .......................... 128/642 |
| 4,641,656 | 2/1987 | Smits ........................................ 607/5 |
| 4,660,571 | 4/1987 | Hess et al. . |
| 4,662,377 | 5/1987 | Heilman et al. . |
| 4,699,147 | 10/1987 | Chilson et al. ......................... 128/642 |
| 4,776,337 | 10/1988 | Palmaz ........................................ 623/1 |
| 4,932,407 | 6/1990 | Williams ..................................... 607/5 |
| 4,998,975 | 3/1991 | Cohen et al. . |
| 5,005,587 | 4/1991 | Scott . |
| 5,010,894 | 4/1991 | Edhag ..................................... 607/122 |
| 5,010,895 | 4/1991 | Maurer et al. ........................... 128/788 |
| 5,016,808 | 5/1991 | Heil, Jr. et al. ........................ 607/119 |
| 5,100,423 | 3/1992 | Fearnot ..................................... 606/45 |
| 5,108,417 | 4/1992 | Sawyer ................................... 606/198 |
| 5,170,802 | 12/1992 | Mehra ..................................... 607/116 |

OTHER PUBLICATIONS

"MR Imaging Artifacts, Ferromagnetism, And Magnetic Torque Of Intravascular Filters, Stents, And Coil"—By: George Teitelbaum, M.D. et al., Radiology, Mar. 1988, pp. 657–663.

"First Clinical Results With A New Caval Filter"—By: Rolf W. Gunther, et al., Cardiovascular And International Radiology, 1987, pp. 104–108.

"Intravascular Stents To Prevent Occulsion And Restenosis After Transluminal Angioplasty"—By: Ulrich Sigwart, Mar. 1987, pp. 701–706.

1980—"Ventricular Defibrillation With Myocardial Electrodes In The Dog, Calf, Pony, And Pig"—By: Jerry H. Gold, Ph.D., et al., Medical Instrumentation, Jan.–Feb. 1980, pp. 19–23.

*Primary Examiner*—William E. Kamm
*Assistant Examiner*—Jeffrey R. Jastrazab
*Attorney, Agent, or Firm*—Haugen and Nikolai

[57] ABSTRACT

Implantable electrode structures for use in apparatus for applying electrical therapy to a patient's heart in the treatment of arrhythmias such as tachycardias and fibrillations of the heart are herein disclosed. The electrode structures are made in the form of expandable (or self-expanding) intravascular stents for insertion through the patient's vascular system to locations in or adjacent the heart. The electrode structures can be inserted into the great veins by insertion techniques used for intravascular stent applications and provide increased electrode surfaces for discharge of electrical energy through the heart in conjunction with other strategically placed electrodes. The wire filament of the stents may be evenly spaced to form a circumferential array or may be non-uniformly spaced to form an elliptical array.

36 Claims, 4 Drawing Sheets

STENT-TYPE DEFIBRILLATION ELECTRODE STRUCTURES

This is a continuation of application Ser. No. 08/243,656 filed May 16, 1994 now abandoned, is a continuation of application Ser. No. 07/955,166 filed Oct. 1, 1992, now abandoned.

BACKGROUND OF THE INVENTION

This invention relates to apparatus for applying electrical pulse treatment to the heart such as for reversing tachycardias and fibrillations of the heart. More particularly, the invention relates to novel forms of electrode structure for use in such apparatus.

It is known to pace, cardiovert and defibrillate the heart using implanted electrodes and such electrodes are currently available in a variety of different constructions. Some such electrodes reside in the heart, some are affixed to the surface of the heart, and others are implanted just beneath the surface of the skin. Examples of such electrodes are disclosed in U.S. Pat. Nos. 3,942,536; 4,291,707 and 4,662,377.

Furthermore, electrodes are known which are intended for temporary residence in veins and arteries. One such example is disclosed in U.S. Pat. No. 4,660,571 which describes a lead suitable for mapping, ablation and/or pacing.

In their simplest form, most two electrode defibrillation/cardioversion lead systems can be modeled as a series of one or more resistors across the output of a signal generator. This model incorporates five series resistors which represent the two electrodes, their conductors and the tissue between the electrodes. These resistors form a voltage divider controlling both the current flowing in the circuit and the voltage drop across each component. Since the purpose of defibrillation is to stimulate tissue, the voltage drop across the conductors and electrode interfaces is wasted energy. Therefore, maximizing defibrillation efficiency is based on minimizing the electrode interface impedance (near field impedance).

The current distribution across an electrode surface is determined by ohmic (field) rather than kinetic (chemical) factors when voltages exceed approximately 30 volts. Thus, the current density around the perimeter or physical extremes of defibrillation electrodes are dramatically higher than at their center. Several consequences result. First, the center of a planar electrode is of marginal significance and can be eliminated with relatively little impact on system impedance. Second, the larger the perimeter of an electrode, the lower the near field impedance of the electrode. This decrease in what is commonly referred to as "interface impedance" increases efficiency by increasing the percentage of the electrical voltage delivered to the tissue. Finally, increasing the separation distance between adjacent active surfaces of the same polarity reduces the electrode's near field impedance by decreasing the current density between surfaces. Thus, within limits (approximately 3 cm), there is an advantage to increasing the separation distance between adjacent electrode surfaces.

It is also known that the distribution of current density with respect to the heart affects the efficiency with which a heart is defibrillated.

SUMMARY OF THE INVENTION

It is an object of the invention to provide an implantable electrode capable of supporting high currents appropriate for heart treatments and for delivering electrical energy to the heart with maximum efficiency.

It is another object of the invention to provide an electrode of the kind described which can be implanted in a major vein and which is capable of supporting current for cardiac pacing, cardioverting and defibrillating without substantially impeding blood flow through the vein.

Another object of the invention is to provide an intravascular electrode structure which can be used in apparatus for applying electrical therapy to the heart, which can be implanted with relative ease and which is suitable for use at various locations in and around the heart dependent on a patient's individual needs and characteristics.

Broadly stated, the present invention provides an electrode structure for use in apparatus supplying electrical therapy to the heart, the electrode structure being in the form of an intravascular stent of electrically conducting material with means for electrically connecting the stent to suitable electrical therapy applying equipment.

A stent electrode structure in accordance with the invention may be implanted intravenously generally in a manner well known per se for stent implantation at a strategic location in or near the heart in a major vein. The stent may be connected via a suitable intravascular conductor to an implanted pulse generator having a further electrode or electrodes associated therewith, that may also comprise one or more additional stent electrodes, intracardiac or intravascular catheter electrodes, patch electrodes or combinations thereof, for applying electrical therapy to the heart.

A stent electrode in accordance with the invention may, for example, be constructed from a surgical-grade stainless steel alloy which is geometrically stable, pliable, and self expanding. Due to its elastic and pliable properties, the diameter of the stent may be substantially reduced by a constraining member for introduction into a vein, the stent returning to its original diameter once the constraining member is removed so as to make intimate contact with the vein wall while allowing blood to flow through the stent substantially unimpeded. Stent structures per se are known in numerous configurations and may be readily adapted for use as a stent electrode structure in accordance with the invention.

It is understood, for the purposes of this application, that a stent electrode structure is an electrically conducting structure of generally tubular form and of expandable diameter. It is contemplated that the stent can be compressed from its relaxed in-use configuration, introduced into the vein, and then permitted to expand toward its relaxed state. Accordingly, stent structures for use in the invention, have a relatively large diameter and reduced length when in place, such diameter being selected in accordance with a vein into which the structure is to be inserted so that when in place, the stent will intimately contact the inner wall of the vein. The structure is such, however, that the diameter can be reduced, correspondingly increasing the length of the stent for insertion through the vein by a catheter or the like in known manner.

Alternatively, the stent diameter may be sized smaller than the vascular system in its relaxed state, and introduced in its relaxed state to its final position. In this case, there is no need to compress the stent for introduction.

The stent electrode comprises a plurality of conductive wires which are spaced from each other at a maximum distance for lowering the interface impedance of the electrode and thus maximizing discharge efficiency.

Furthermore, because stent electrode structures according to the invention can be made to any suitable length and diameter without impeding blood flow, they can provide electrodes of larger surface area than known implantable electrodes, therefore being more able to support the currents needed for supplying electrical shock therapy to the heart.

Exemplary stent structures which are particularly suitable for use in the invention will be described below with reference to the accompanying drawings.

DESCRIPTION OF PREFERRED EMBODIMENTS

Figure 1:
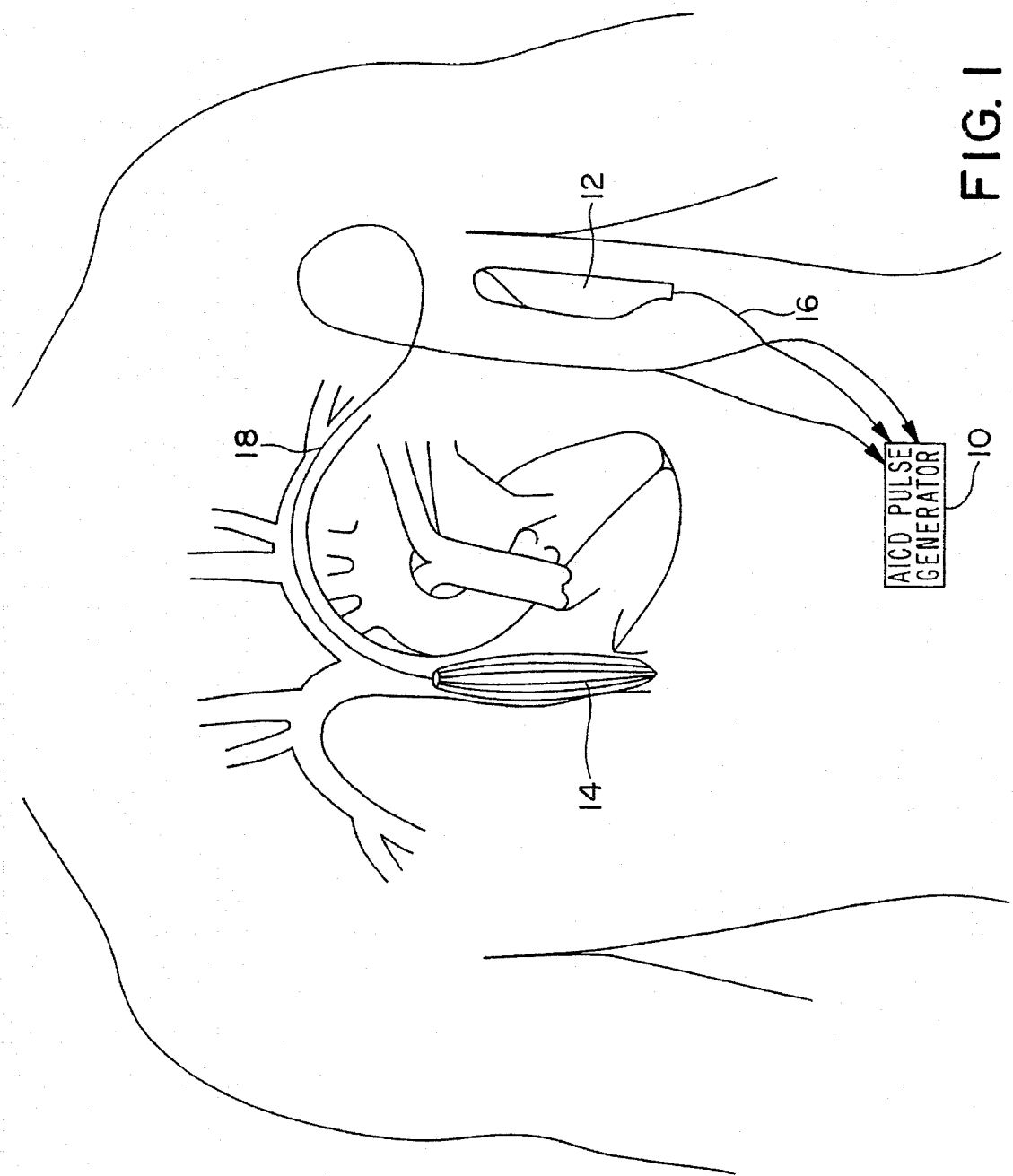
FIG. 1 is a diagrammatic view of apparatus in accordance with the invention implanted in a patient for applying electrical therapy to the heart in the treatment of tachycardia and fibrillations, such apparatus including a single stent electrode structure.

FIG. 1 shows apparatus for applying electrical therapy to the heart, for example, in the case of a tachycardia or fibrillation, such apparatus comprising a known form of implanted pulse generator 10 and implanted electrodes 12 and 14 connected to the pulse generator by respective conductors 16 and 18. Electrode 12 may, for example, comprise a known form of subcutaneous patch electrode structure, or may alternatively comprise a subclavian electrode. Electrode 14, on the other hand, comprises an intravascular stent electrode structure, in accordance with the invention, which in the illustrated example of FIG. 1 is inserted in the inferior vena cava (IVC). The configuration of the stent electrode structure is such that in its radially expanded condition, the diameter of the structure substantially corresponds with the diameter of the IVC whereby the periphery of the electrode is in contact with the interior wall of the IVC, while the nature of the stent structure still allows for substantially unimpeded blood flow through the IVC.

Figure 3:
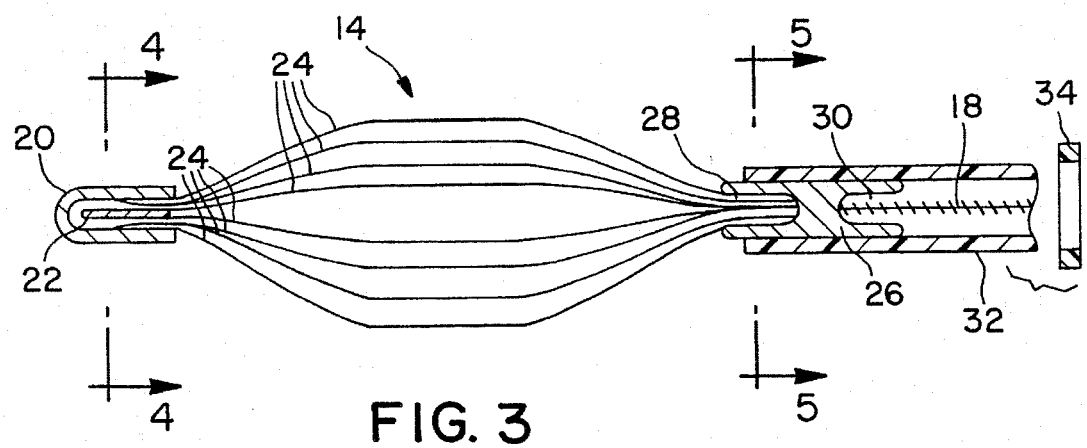
FIG. 3 is a sectional side elevational view of a distal stent electrode structure in accordance with the invention.
Figure 4:
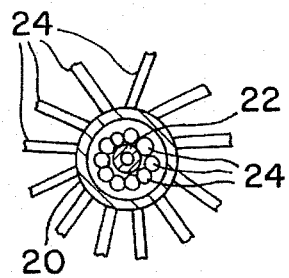
FIG. 4 is a sectional view on line 4—4 of FIG. 3.
Figure 5:
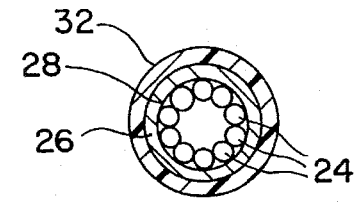
FIG. 5 is a sectional view on line 5—5 of FIG. 3.

While numerous known forms of stents or emboli filters may be used to form the electrode structure 14, for example, woven or braided stent structures, a particularly useful form of electrode structure is illustrated in FIGS. 3-5. Referring, therefore, in more detail, to FIGS. 3-5, the stent structure 14, referred to as a distal stent electrode, comprises a distal crimp tube 20 which forms a first end of the distal electrode. The distal crimp tube 20 may have an outer diameter of about 0.070 inches and acts as an end point for the distal electrode structure denoting the furthest point that the distal electrode reaches into the vein. Within the distal crimp tube 20 is an inner crimp tube 22. The inner crimp tube 22 may allow the distal crimp tube to temporarily secure a stylet wire (not shown) used for placing the electrode in the proper position in the vein. Between the respective crimp tubes, are positioned a circular array of parallel electrode wires 24 which are crimped between the tubes. The wires typically number between 3-12 and may be constructed of MP35N coated with platinum. The wires preferably are pre-bent to assume a basket-like configuration in their relaxed state as shown in FIG. 3 with an outer diameter greater than the diameter of the crimp tube 22, but the wires may be radially resiliently compressed in the manner of a stent to allow insertion through the vein. In the relaxed radially expanded state, the wires allow substantially unimpeded blood flow through the electrode structure.

Secured to the opposite end of the wires 24 is a proximal crimp tube 26 having a like diameter to tube 20. Again, the wires 24 are suitably crimped in a blind bore 28 at the forward end of the crimp tube 26. The conductor 18 (or a lead for connection to conductor 18) may be suitably crimped in a further blind bore 30 at the proximal end of crimp tube 26. The crimp tube 26 and the conductor 18 may be covered by a suitable insulating sheath 32. For the sake of clarity, FIG. 5 shows the individual wires 24 being spaced around the circumference of the blind bore in crimp tube 26. It will be understood, however, that when the wires are crimped within the blind bore, they will be closely bunched together. The outer diameter of the wires in their relaxed shape need not be greater than the diameter of the crimp tubes 22 and 26.

Reverting to FIG. 1, the electrodes 12 and 14 are strategically placed relative to the heart to provide an electrical field encompassing the heart upon receipt of electrical pulses from the generator 10. In order to position electrode 14 within the IVC as illustrated, or in another suitable intravascular location, the electrode may be placed within a constraining catheter (introducer) 34 or the like to reduce its diameter and may be introduced to the vein. Upon removal of the catheter, the electrode expands to its natural diameter contacting the interior wall of the vein while allowing substantially unimpeded blood flow. Alternatively, the stent may be introduced in its relaxed state via a balloon catheter or the like, if it is the version sized smaller than the vascular system, in relaxed state. To implant the electrode, standard cut-down techniques to expose the vein may be used. A guide wire may be passed into the inferior vena cava to the level of the diaphragm once the vein is exposed. An introducer and dilator may then be introduced over the guide wire to the same depth as the guide wire. The guide wire and dilator may be removed and the electrode catheter positioned through the introducer to a position distal to its final position. The introducer is then removed and the catheter is moved to its final position. Dependent on the strength and number of electrode filaments in the catheter, a stylet wire may be needed to position the distal end of the distal electrode. In this case, the stylet wire is temporarily secured to the distal crimp tube to place the electrode in position and crimp tube 26 would incorporate a through hole. The electrode 12 and pulse generator 10 may be subcutaneously inserted into the patient in a well known manner.

The distal stent electrode 14 shown in FIG. 1, may conveniently be located in the SVC/IVC extending from above the plane of the top of the atrium to below the plane of the RV apex.

Figure 2:
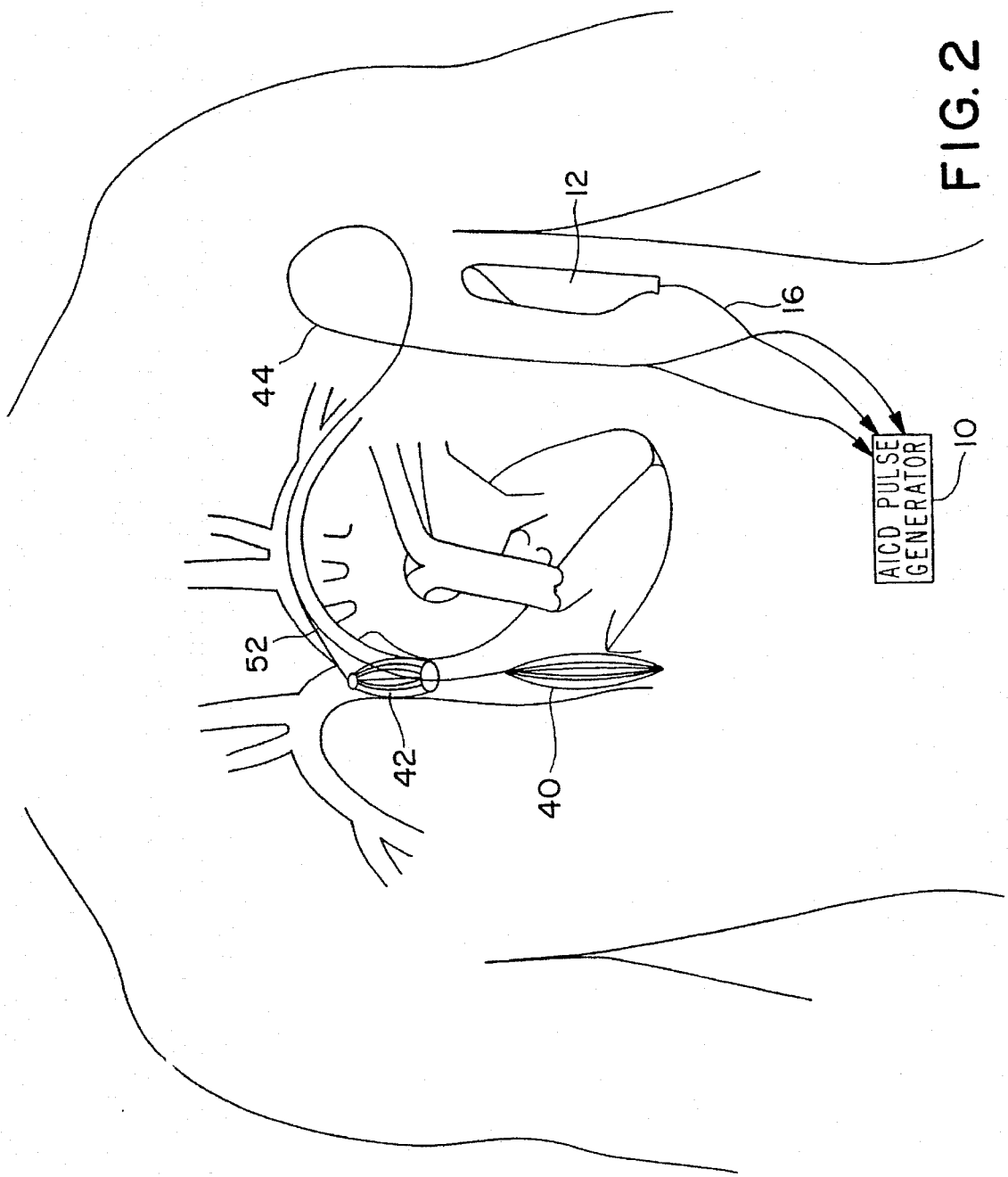
FIG. 2 is a view similar to FIG. 1 showing apparatus in accordance with the invention having a plurality of strategically located stent electrode structures.

Another arrangement in accordance with the invention is shown in FIG. 2 where two stent electrode structures 40 and 42 are used in combination with the pulse generator 10 and subcutaneous patch electrode 12. The electrode structure 40 in FIG. 2 may be a distal-type electrode as illustrated in FIGS. 3-5, and may be connected to the pulse generator through lead 44. This electrode may be positioned with its distal end at the same level as the RV apex. The second electrode 42 may be a somewhat smaller electrode structure, referred to as a proximal stent electrode structure and having a construction shown, for example, in FIGS. 6 and 7.

Figure 7:
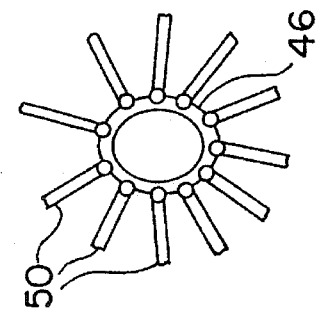
FIG. 7 is a sectional view on line 7—7 of FIG. 6.
Figure 6:
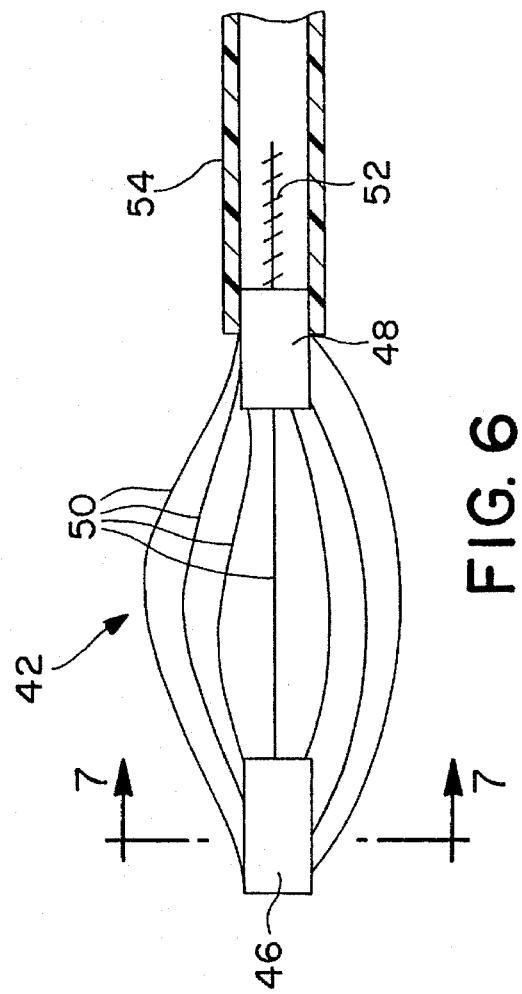
FIG. 6 is a sectional elevational view of a proximal stent electrode structure in accordance with the invention.

The structure shown in FIGS. 6 and 7 comprises a pair of spaced ring electrodes 46, 48 interconnected by a circumferential array of wire filaments 50 which may again be MP35N coated with platinum. The respective wires may be welded to the ring electrodes 46 and 48 and to this end the ring electrodes may include circumferential grooves to receive the wires and minimize damage to a vein wall when the electrode structure is inserted. As in the previously described electrode structure, the wires 50 preferably are pre-shaped to have a radially expanded basket-like configuration as shown in FIG. 6 so as to intimately contact the vein wall while allowing unimpeded blood flow through the electrode. The wires, however, can be resiliently compressed for insertion of the electrode in like manner to the insertion techniques previously described. The ring electrode 48 may be connected to a suitable conductor 52 with a sheath 54 of silicon rubber or the like. The conductor 52 will be suitably connected to the pulse generator 10 in like manner to the conductors 16 and 44. The electrode structures 40 and 42 and their associated conductors 44 and 52 may be carried in the same or separate lead bodies and may be inserted by the techniques previously described. In the arrangement shown in FIG. 2, for example, the electrode 40 may be positioned with its distal end at the same level as the RV apex and the electrode 42 may be positioned in the superior vena cava.

The arrangement shown in FIG. 2, may be used, for example, where a more comprehensive electric field encompassing the heart is required as compared with the arrangement shown in FIG. 1.

Figure 8:
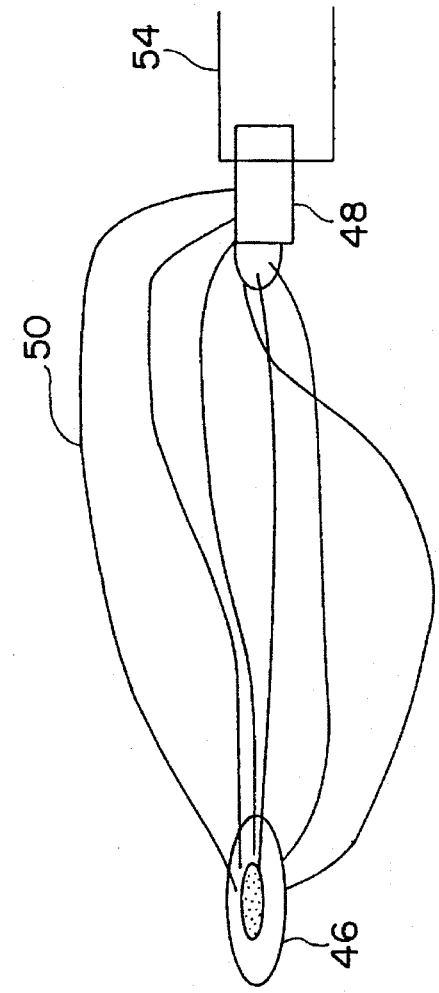
FIG. 8 is a perspective view of a modification to the electrode shown in FIGS. 6 and 7.

FIG. 8 illustrates a modification to the electrode shown in FIGS. 6 and 7. Specifically, one end of each of the wire filament electrodes is twisted or bent along the longitudinal axis of the electrode so that the filaments as a group are twisted about the longitudinal axis. Also, the filaments may be bent so that the ring electrodes 46 and 48 are not coaxial with one another. This is useful in focusing discharge in a particular direction. The electrodes of FIGS. 1–5 may be modified in a similar manner.

Figure 9:
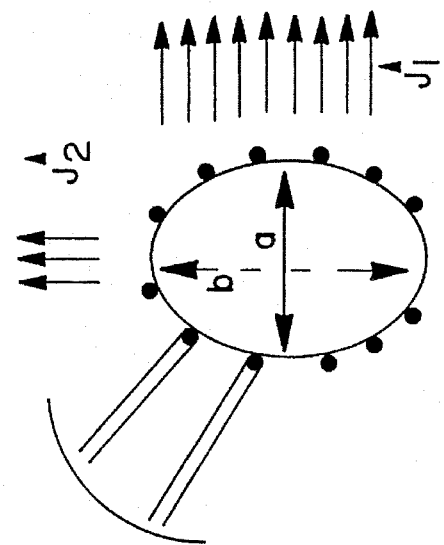
FIG. 9 is a cross-sectional view of a further modification of the stent electrode according to the present invention.

FIG. 9 illustrates another modification in which the electrode has non-circularly symmetric geometry. That is, the electrodes 14, 40 and 42 may have an elliptical cross-section with a minor axis a and a minor axis b. The wire filaments are not uniformly spaced. There is a greater number, and hence, density of conductive wire filaments along the major axis b. Therefore, a greater current flow of current density $J_1$ will be generated perpendicular to the major axis than the current density $J_2$ perpendicular to the minor axis. This is advantageous if it is desired to focus current density in a particular direction corresponding to the major axis.

It will be evident from the above, that the invention comprises the use of an expandable electrode similar to a vascular stent or emboli filter for applying electrical pulses to the heart in the treatment of arrhythmias such as tachycardias or fibrillations. The electrode structures may take the form of those described above. Alternatively, other known stent structures may be used, such as woven, braided or expanded rolled corrugated sheet structures. The electrodes may be positioned in one of the great veins or arteries by use of an insertion system including guide wires, vein dilators, vein introducers, using a femoral approach or a subclavian approach according to techniques well known per se in the art. The electrodes may be positioned in the inferior vena cava, the superior vena cava, the cephalic vein or any of the heart chambers.

The foregoing description is intended by way of example only and is not intended to limit the present invention in any way except as set forth in the following claims.

We claim:

1. In an apparatus for applying electrical therapy to a patient's heart for treatment of cardiac arrhythmias, including tachycardias and fibrillations, comprising pulse generator means for generating pulses, at least two electrode structures implantable within the patient's body, and means, electrically connecting the at least two electrode structures to the pulse generator means, for discharging electricity through the heart in response to pulses generated by the pulse generator means, the improvement wherein at least one of said electrode structures comprises an expandable electrically conducting intravascular stent for location in or adjacent the heart and providing substantially unimpeded blood flow therethrough when positioned in the vascular system, the stent comprising an array of substantially linear wire filaments and end members interconnecting the filaments at opposite ends thereof, the filaments being shaped into a radially compressible basket-like configuration.

2. The improvement as defined in claim 1, wherein the wire filaments are non-uniformly spaced.

3. The improvement as defined in claim 2, wherein the wire filaments are arranged in an elliptical array having a major axis and a minor axis, a greater number of wire filaments being disposed along the major axis than the minor axis so as to focus greater current density perpendicular to the major axis.

4. The improvement as defined in claim 1, wherein said end members comprise a distal end crimp tube surrounding the wire filaments at one end thereof and a proximal end crimp tube surrounding the wire filaments at an opposite end thereof.

5. The improvement as defined in claim 4, further including an inner crimp tube within the distal end crimp tube, with respective ends of the wire filaments being trapped between the distal end crimp tube and the inner crimp tube.

6. The improvement as defined in claim 4, wherein the proximal end crimp tube is attached to an electric conductor for connecting the at least one of said electrode structures to the pulse generator means.

7. The improvement as defined in claim 6, wherein the proximal end crimp tube has a first blind bore receiving respective ends of the wire filaments and a second blind bore receiving the electric conductor.

8. The improvement as defined in claim 1, wherein the end members comprise respective ring electrodes and respective ends of the wire filaments have weld connections with the ring electrodes.

9. The improvement as defined in claim 8, wherein the ring electrodes have external grooves receiving the respective ends of the wire filaments and said weld connections.

10. The improvement as defined in claim 1, wherein said at least two electrode structures comprise intravascular stent structures.

11. The improvement as defined in claim 10, wherein each of said at least two electrode structures comprises an array of wire filaments and end members interconnecting the wire filaments at opposite ends thereof, the wire filaments being shaped into at least two radially compressible basket-like configurations.

12. The improvement as defined in claim 11, wherein the wire filaments are non-uniformly spaced.

13. The improvement as defined in claim 12, wherein the wire filaments are arranged in an elliptical array having a major axis and a minor axis, a greater number of wire filaments being disposed along the major axis than the minor axis so as to focus greater current density perpendicular to the major axis.

14. The improvement as defined in claim 11, wherein one of said at least two electrode structures comprises a distal electrode structure wherein the end members comprise crimp tubes in which respective ends of the wire filaments are trapped and the other of said at least two electrode structures comprises a proximal electrode structure wherein the end members comprise ring electrodes to which respective ends of the wire filaments are welded.

15. The improvement as defined in claim 11, wherein each of the at least two electrode structures has an electrical conductor lead for connecting the at least two electrode structures to the pulse generator means, said leads being contained in a common lead body.

16. The improvement as defined in claim 1, wherein the stent is resiliently compressible radially for insertion thereof through the patient's vascular system and radially expandable into contact with a vein wall in the vascular system.

17. The improvement as defined in claim 16, and further comprising means for positioning the stent in the patient's SVC/IVC extending from above the plane of the patient's atrium to below the plane of the patient's RV apex.

18. An apparatus for applying electrical therapy to a patient's heart for the treatment of cardiac arrhythmias, including tachycardias and fibrillations, comprising:

pulse generator means, adapted to be subcutaneously inserted in the patient's body, for generating pulses; and at least two electrode structures connected to the pulse generator means by respective electrical conductors, the electrode structures adopted to be implanted within the patient's body for discharging electrical energy through the patient's heart in response to pulses generated by the pulse generator means;

wherein at least one of the electrode structures comprises an expandable electrically conducting intravascular stent, the stent being adopted to be in contact with an inner wall of said passage and providing substantially unimpeded blood flow through the passage and wherein the stent comprises an array of substantially linear wire filaments and end members connecting opposite ends of the wire filaments, the wire filaments being shaped into a basket-like configuration.

19. An apparatus as defined in claim 18, wherein the wire filaments are non-uniformly spaced.

20. An apparatus as defined in claim 18, wherein the wire filaments are arranged in an elliptical array having a major axis and a minor axis, a greater number of wire filaments being disposed along the major axis than the minor axis so as to focus greater current density perpendicular to the major axis.

21. An apparatus as claimed in claim 18, wherein the wire filaments are twisted between said end members about an axis passing between said end members.

22. An apparatus as claimed in claim 18 wherein said at least two electrode structures include a first stent electrode adopted to be positioned with a distal end thereof level with the patient's RV apex, a second smaller stent electrode adopted to be positioned in the patient's SVC, and a third patch electrode for discharging with the stent electrodes.

23. An apparatus as defined in claim 27, wherein each stent electrode comprises a circumferential array of said wire filaments and end members connecting the respective ends of the wire filaments.

24. An apparatus as claimed in claim 22, wherein the wire filaments are twisted between said end members about an axis passing between said end members.

25. An apparatus as defined in claim 18, wherein the end members comprise crimp tubes in which the respective ends of the wire filaments are trapped.

26. An apparatus as defined in claim 25, wherein the crimp tubes have respective blind bores in which the ends of the wire filaments are trapped, and one of the crimp tubes has a further blind bore for receiving an electrical conductor.

27. An apparatus as defined in claim 26, wherein another of the crimp tubes includes an inner crimp tube within one of the respective blind bores and respective ends of the wire filaments are arranged around the inner crimp tube.

28. An electrode structure for use in a patient-implanted apparatus for applying electrical therapy to a patient's heart, the electrode structure comprising:

an electrically conducting expandable intravascular stent having a circumferential array of wire filaments; and end members respectively connecting opposite ends of the wire filaments, the filaments having a basket-like shape;

wherein the end members comprise ring electrodes and the filaments have weld connections with said ring electrodes.

29. A device for use in applying electrical therapy to a patient's heart, the device comprising:

an intravascular stent having a circumferential array of electrically conductive filaments and end members interconnecting the filaments at opposite proximal and distal ends thereof, the filaments being shaped into a radially compressible basket-like configuration;

an electrical conductor having a proximal end and a distal end, and a means for electrically coupling the distal end of the electrical conductor with the proximal ends of the filaments; and a catheter positioned in surrounding relation to the filaments to radially compress the filaments and maintain the filaments radially compressed to facilitate use of the catheter in delivering the stent to a predetermined intravascular location, the catheter further being removable proximally from the stent to allow the filaments to resiliently self-expand toward the basket-like configuration and into intimate contact with a vascular wall at the predetermined location.

30. The device of claim 29 further including:

an electrically insulative sheath mounted near the proximal ends of the filaments and extending proximally away from the stent in surrounding relation to the conductor.

31. The device of claim 29 wherein:

the filaments are substantially linear.

32. The device of claim 29 wherein:

the filaments when in the basket-like configuration are spaced apart from one another, over most of their lengths between their proximal and distal ends, a distance sufficient to decrease a current density between surfaces of adjacent filaments and at most approximately 3 cm.

33. The device of claim 29 wherein:

the spacing between adjacent ones of the filaments over the majority of a span of filaments between the end members, with the filaments in the basket-like configuration, is approximately 3 cm.

34. An electrode structure positionable at an intravascular location near the heart for applying electrical therapy to the heart; the electrode structure including:

an array of electrically conductive filaments and end members interconnecting the filaments at opposite proximal and distal ends thereof, the filaments being shaped into a basket-like configuration in which a separation distance between adjacent ones of the filaments, over most of the filament lengths between said opposite ends, is sufficient to decrease the current density between surfaces of the adjacent filaments and is at most approximately 3 cm; and an electrically conductive pulse delivery path, coupled to the proximal ends of the filaments, for delivering electrical pulses to all of the filaments simultaneously;

wherein the filaments are radially compressible from the basket-like configuration to facilitate intravascular delivery of the array to a predetermined intravascular location, and after said delivery are expandable toward the basket-like configuration into intimate contact with a vascular wall at the predetermined intravascular location.

35. The electrode structure of claim 34 wherein:

said separation distance is approximately 3 cm.

36. The electrode structure of claim 34 wherein:

the filaments are substantially linear.

* * * * *

UNITED STATES PATENT AND TRADEMARK OFFICE
CERTIFICATE OF CORRECTION

PATENT NO. : 5,531,779
DATED : July 2, 1996
INVENTOR(S) : Roger W. Dahl, et al

It is certified that error appears in the above-indentified patent and that said Letters Patent is hereby corrected as shown below:

Claim 18, column 7, line 34 "adopted" should read
-- adapted --; line 40 "adopted" should read
-- adapted --.

Claim 22, column 7, line 60 "adopted" should read
-- adapted --; line 62 "adopted" should read -- adapted --.

Claim 23, column 7, line 64 "27" should read -- 22 --.

Signed and Sealed this

First Day of October, 1996

Attest:

BRUCE LEHMAN

*Attesting Officer*  *Commissioner of Patents and Trademarks*